United States Patent [19]
Harris et al.

[11] Patent Number: 6,018,078
[45] Date of Patent: Jan. 25, 2000

[54] STABILIZED N-NITROSOHYDROXYLAMINES

[75] Inventors: Darrell V. Harris, Ocean Springs, Miss.; Paul J. Roman, Jr., North Tonawanda, N.Y.; Zhihong Wu, Pascagoula, Miss.; Earl G. Adams, Grand Bay, Ala.; Eric L. Williams, Pascagoula, Miss.

[73] Assignee: First Chemical Corporation, Pascagoula, Miss.

[21] Appl. No.: 09/338,786

[22] Filed: Jun. 23, 1999

[51] Int. Cl.[7] .................................................. C07C 209/90

[52] U.S. Cl. ........................................ 564/6; 5/112; 5/113

[58] Field of Search .................................. 564/5, 6, 112, 564/113

[56] References Cited

U.S. PATENT DOCUMENTS

| | | | |
|---|---|---|---|
| 3,426,063 | 2/1969 | Gros | 260/666.5 |
| 4,144,260 | 3/1979 | Zoller et al. | 260/498 R |
| 4,638,079 | 1/1987 | Inskip et al. | 560/4 |
| 4,692,544 | 9/1987 | Goerner et al. | 560/4 |
| 4,772,740 | 9/1988 | Varwig | 252/180 |
| 4,898,976 | 2/1990 | Varwig | 252/404 |
| 4,980,079 | 12/1990 | Yamato et al. | 560/4 |
| 5,034,156 | 7/1991 | Varwig | 252/403 |
| 5,292,920 | 3/1994 | Upmacis et al. | 560/4 |

*Primary Examiner*—Peter O'Sullivan
*Attorney, Agent, or Firm*—Alston & Bird LLP

[57] ABSTRACT

N-nitrosohydroxylamine compounds exhibiting minimal or no degradation are disclosed. The N-nitrosohydroxylamines can be stabilized in the presence of a compound capable of removing water from the environment.

42 Claims, No Drawings

STABILIZED N-NITROSOHYDROXYLAMINES

FIELD OF THE INVENTION

The present invention relates to N-nitrosohydroxylamine compounds useful as polymerization inhibitors, and more particularly, to stabilized N-nitrosohydroxylamine compounds.

BACKGROUND OF THE INVENTION

N-nitroso-N-hydroxylamine salts, such as N-nitroso-N-phenylhydroxylamine aluminum complexes (also referred to generally as NPAL), are used as polymerization inhibitors or stabilizers in a variety of polymerization systems. For example, NPAL can be used as a stabilizer in free radical polymerization systems (such as used to polymerize olefins, unsaturated polyesters, styrene, acrylates, and the like). NPAL acts to prevent premature polymerization and the attendant problems of increased viscosity/gelling, loss of reactivity of the monomer/oligomer, etc. NPAL and similar compounds can also be used in other types of polymerizations systems, such as those initiated by exposure to radiation (such as UV curable systems), thermally initiated polymerization systems, and others.

Despite its usefulness as a polymerization inhibitor, there are problems associated with the use of NPAL. Specifically NPAL and other N-nitrosohydroxylamine compounds are unstable and undergo degradation, as manifested by discoloration and formation of a precipitate in some instances. The precipitate which is formed is insoluble in all polymerization systems causing turbid mixtures. In addition, the degradation can result in a loss of effectiveness of NPAL as a polymerization inhibitor. Further, customers are reluctant to use the product once it darkens, and the product cannot be readily used in color sensitive applications.

Prior attempts to stabilize NPAL, e.g., to minimize the extent and rate of degradation, include storing the product in a dark (amber) container under an inert atmosphere (nitrogen blanket). In addition, typically NPAL is shipped and stored under cold conditions, generally being refrigerated until used. This, however, can be costly.

U.S. Pat. No. 4,898,976 to Varwig describes the degradation of such compounds, and in particular cupferron (the ammonium salt of N-nitroso-phenylhydroxylamine) as a result of the instability of solutions thereof in the presence of air. To address the degradation of cupferron, the '976 patent reports the use of an ethanolamine salt of N-nitrosophenylhydroxylamine.

SUMMARY OF THE INVENTION

The present invention provides stabilized N-nitrosohydroxylamine compounds exhibiting desirable properties, such as minimal or no change in color and/or toluene insolubles content after being stored. Exemplary N-nitrosohydroxylamine compounds which can be stabilized in accordance with the invention include metallic complexes or metal salts of N-nitrosohydroxylamines. As used herein, the terms "metal salts" and "metallic complexes" are synonymous and include all salts and complexes. Particularly preferred stabilized compounds include metal salts of N-nitrosohydroxylamines, such as N-nitroso-N-phenylhydroxylamine aluminum complex.

To stabilize the N-nitrosohydroxylamine compounds, the N-nitrosohydroxylamine compound is placed in the presence of at least one stabilizing agent comprising a substance capable of adsorbing and/or absorbing moisture and/or other vapors. Although not wishing to be bound by any explanation of the invention, it is currently believed that the instability of N-nitrosohydroxylamine complexes is caused at least in part by water. Specifically, the inventors have found that when exposed to water, N-nitrosohydroxylamine metal complexes react with water molecules in the atmosphere to form undesirable byproducts. For example, NPAL can form a dimer on reaction with water (composed of four N-nitrosohydroxylamine ligands, two aluminum atoms and two hydroxy ligands), also referred to as an aluminohydride complex, which is insoluble, rendering NPAL unfit for its intended use over time. The formation of this dimer releases free N-nitrosohydroxylamine molecules which, in turn, rapidly decompose producing the darkening of the product. While not wishing to be bound by any theory or explanation of the invention, it is also currently suspected that the stabilizing agents also function by absorbing and/or adsorbing other vapors such as nitrogen oxides which may be present.

Exemplary stabilizing agents include molecular sieves, activated carbon, hygroscopic sulfate salts, silica and mixtures thereof. Currently preferred stabilizing agents include molecular sieves, activated carbon and mixtures thereof.

The invention also provides packages or containers of stabilized N-nitrosohydroxylamine compounds in which the stabilizing agent has been placed. Advantageously, the stabilizing agent is placed in the container of N-nitrosohydroxylamine in a smaller, separate container, which is porous to the passage of moisture in the container environment. The desiccated containers can be readily shipped and stored without requiring refrigeration over extended periods of time.

DETAILED DESCRIPTION OF THE INVENTION

The present invention now will be described more fully in the following detailed description, in which preferred embodiments of the invention are described. This invention may, however, be embodied in many different forms and should not be construed as limited to the embodiments set forth herein; rather, these embodiments are provided so that this disclosure will be thorough and complete, and will fully convey the scope of the invention to those skilled in the art.

N-nitrosohydroxylamine compounds which can be stabilized in accordance with the present invention include any of the types of N-nitrosohydroxylamine metal complexes thereof as known in the art. N-nitrosohydroxylamines can be generally represented by the formula

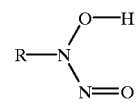

which may be in equilibrium with the tautomeric amine oxide form:

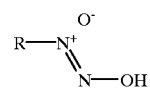

wherein each R is independently selected from the group consisting of alkyl, substituted alkyl, aryl and substituted aryl.

Metal complexes of N-nitrosohydroxylamines which may be employed as inhibitors are also well known compounds, and may have the following formula:

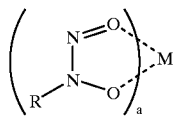

wherein:
  each R is independently selected from the group consisting of alkyl, substituted alkyl, aryl and substituted aryl;
  M is a metal; and
  a is 1 to 4, and is a number equal to the valence of M.

As used herein, the term "alkyl" means straight or branched chain hydrocarbon, typically having 1 to 20 carbon or cyclic hydrocarbon typically having 3 to 20 carbon atoms. Cyclic hydrocarbon includes one or more cyclic hydrocarbon rings. "Substituted alkyl" is alkyl having one or more substituents. "Aryl" means one or more aromatic rings, each of 5 or 6 carbon atoms. Multiple aryl rings may be fused, as in naphthyl or unfused, as in biphenyl. "Substituted aryl" is aryl having one or more substituents. Suitable substituents or radicals include, but are not limited to, halo, —OH, —CN, C1–C10 alkyl, C2–C10 alkenyl, C2–C10 alkynyl, C1–C10 alkoxy, C7–C12 aralkyl, C7–C12 alkaryl, C3–C10 cycloalkyl, C3–C10 cycloalkenyl, and the like. Preferably R is aryl, and more preferably phenyl or naphthyl.

Examples of specific N-nitrosohydroxylamine compounds include without limitation N-nitrosophenylhydroxylamine, N-nitroso-1-napthylhydroxylamine, and the like and mixtures thereof. Other specific compounds include N-nitroso-p-chlorophenylhydroxylamine or the bromo compound.

Examples of salts of the above N-nitrosohydroxylamines which may be used include metal salts. Exemplary metal salts include without limitation alkali metal salts, such as potassium or sodium salts; alkali earth metal salts, such as magnesium and calcium salts; Group IIIA salts, such as aluminum salts; Group IVA salts such as tin salts; Group IB salts, such as copper salts; Group VIII salts such as iron, cobalt, and nickel salts; Group IVB salts, such as titanium salts; Group VB salts, such as vanadium salts; Group VIB salts, such as molybdenum salts; Group VIIB salts, such as manganese salts; and the like and mixtures thereof. An exemplary salt is N-nitroso-N-phenylhydroxylamine aluminum complex.

N-nitrosohydroxylamines and salts thereof can be prepared using processes known in the art and/or are commercially available. Metal salts of N-nitrosohydroxylamine can be readily prepared through ion-exchange of N-nitrosohydroxylamine or salt thereof with the intended metal. For example, NPAL can be prepared by reacting an aluminum salt, such as aluminum sulfate, with N-nitroso-N-phenylhydroxylamine ammonium salt, although other salts, such as halides, phosphates, nitrates, carbonates, and organic acid salts of the metal can also be used.

Methods of making and using N-nitrosohydroxylamines useful in the invention are described, for example, in U.S. Pat. Nos. 3,426,063; 4,144,260; 4,980,079; 4,638,079; 4,898,976; and 5,292,920, the entire disclosure of each of which is hereby incorporated by reference.

As used herein, the term "stabilized N-nitrosohydroxylamines" refers to N-nitrosohydroxylamines which exhibit essentially no or minimal color change when stored at a temperature of 60° C. for 90 days. Color change can be determined by measuring the increase in Gardner color of a 5% solution of the sample in toluene. The color for stabilized NPAL typically ranges from about 1.0 to about 4.0 and preferably the color determined using the Gardner Index scale is no greater than about 2.5. Unstabilized NPAL held for 90 days at 60° C. in a sealed container typically shows an increase in Gardner color of 13 to 15 scale units. The stability of the N-nitrosohydroxylamines can also be determined by measuring toluene insolubles after being stored at a temperature of 60° C. for 90 days. Unstabilized NPAL typically produces 40% to 60% of its original weight in toluene insolubles; whereas, stabilized NPAL typically produces no toluene insolubles. Advantageously the stabilized N-nitrosohydroxylamines of the invention have essentially or substantially no toluene insolubles after being stored at a temperature of 60° for 90 days.

The N-nitrosohydroxylamines are stabilized in accordance with the present invention using an agent capable of stabilizing the N-nitrosohydroxylamine salt, i.e., an agent suitable for preventing or minimizing color change and/or the formation of insolubles as described above. The stabilizing agents can also be defined as agents which are capable of adsorbing, absorbing or otherwise binding water in the atmosphere. In addition, as noted above, the stabilizing agents may be capable of absorbing, adsorbing or otherwise binding other vapors. This in turn can protect the N-nitrosohydroxylamine compound, for example, from reacting with water to form the dimer. Thus, generally the stabilizing agents may be hygroscopic substances (or desiccants), which are capable of adsorbing moisture or water vapor from the air.

Exemplary stabilizing agents in accordance with the invention include without limitation molecular sieves, activated carbon, sulfate salts, silica, and the like as well as mixtures thereof. However, any of the types of substances known in the art which are capable of adsorbing and/or absorbing moisture and/or other vapors from the atmosphere in an amount sufficient to stabilize the N-nitrosohydroxylamine salts can be used in accordance with the invention.

Activated carbon is well known and can be generally described as an amorphous form of carbon characterized by high adsorptivity for many gases, vapors, and colloidal solids. The carbon can be obtained by the destructive distillation of wood, nut shells, animal bones or other carbonaceous material. The carbon is then activated by heating (for example to a temperature of 800 to 900° C.), with steam or carbon dioxide, which results in a porous internal structure.

Molecular sieves are also well known and can be generally described as a microporous structure comprising either crystalline aluminosilicates, chemically similar to clays and feldspars and belonging to a class of materials known as zeolites, or crystalline aluminophosphates derived for example from mixtures containing an organic amine or quaternary ammonium salts. Pore sizes can vary and typically range from about 5 to about 10 Å, although sizes outside of this range can also be useful. These materials can undergo dehydration with little or no change in the crystalline structure and the dehydrated crystals are interlaced with regularly spaced channels of molecular dimensions, which can comprise almost 50% of the total volume of the crystals. As is known in the art, the empty cavities in activated molecular sieve crystals have a strong tendency to recapture water molecules. Such crystals are known as "molecular sieves" because only those molecules that are small enough to pass through the pores of the crystals can enter the cavities and be adsorbed on the interior surface.

Representative sulfate salts include without limitations sulfate salts selected from the group consisting of calcium sulfate, magnesium sulfate, aluminum sulfate, sodium sulfate, and the like and mixtures thereof.

In use, the N-nitrosohydroxylamine compound is packaged in the presence of the stabilizer to minimize and/or prevent substantial degradation of the N-nitrosohydroxylamine compound prior to use, i.e., to maintain a dry atmosphere in the N-nitrosohydroxylamine environment (container). Preferably the stabilizing agent is packaged with the N-nitrosohydroxylamine so that the stabilizing agent can be readily removed from the N-nitrosohydroxylamine. For example, the stabilizing agent can itself be packaged in material having a sufficient porosity to allow the passage of atmospheric water but not the stabilizing agent itself, and the package placed in the environment of the N-nitrosohydroxylamine compound so that the stabilizing agent can act to bind water in this environment. Thereafter, the stabilizing agent can be readily removed and the N-nitrosohydroxylamine compound used as desired.

The resultant package or container of N-nitrosohydroxylamine compound and stabilizing agent can be prepared, shipped and stored for extended periods of time (up to at least three months at ambient temperatures). Thus the invention provides economies of manufacture and use of the product because the N-nitrosohydroxylamine does not have to be refrigerated during shipping and storage. In addition, the shelf life of the product can be extended and less waste can be observed because loss of product resulting from degradation is minimized or eliminated.

The amount of stabilizing agent used in accordance with the invention can vary, depending upon a variety of factors, such as the nature of the N-nitrosohydroxylamine compound, the stabilizing agent, the water or moisture content of the environment of the N-nitrosohydroxylamine compound, temperature, length of storage, and the like. Typically, the stabilizing agent can be present in amounts ranging from about 0.1 to about 25% by weight, preferably from about 0.5 to about 5% by weight, based on the weight of the N-nitrosohydroxylamine.

The stabilized N-nitrosohydroxylamine salts are useful as polymerization inhibitors in a variety of polymerization systems, including without limitation free radical, radiation and thermally initiated polymerization systems. The stabilized N-nitrosohydroxylamine metal salts can be present in the polymerizable composition in conventional polymerization inhibiting amounts as known in the art. As known in the art, typically polymerization systems include one or more ethylenically unsaturated compounds, including monomers, oligomers, and resins. Exemplary polymerizable compounds include without limitation monomers and oligomers derived from acrylic and methacrylic acid; unsaturated polyester resins; unsaturated polyurethane resins, unsaturated epoxy resins; and the like. The polymerizable compounds are used in amounts known in the art, and are optionally dispersed or dissolved in a suitable solvent that is copolymerizable therewith.

The polymerization systems also typically include one or more polymerization initiators. Such systems are well known in the art and include, for example, free radical polymerization initiators such as hydrogen peroxide, the ketone peroxides, diacyl peroxides, the peresters, the perketals, and dialkyl peroxides; radiation polymerization initiators such as benzophenone, thioxanthone and derivatives thereof; and thermal polymerization initiators such as AIBN. The initiators are also used in amounts known in the art.

Unsaturated polyester resins are known in the art, and may be obtained by reaction of approximately equivalent amounts of a polyvalent alcohol such as ethylene glycol, diethylene glycol, triethylene glycol, trimethylene glycol, propylene glycol, pentaerythritol, and other diols or polyols with an unsaturated dibasic carboxylic acid or carboxylic anhydride such as maleic acid, maleic anhydride, fumaric acid, itaconic acid, or citraconic acid. These unsaturated dibasic carboxylic acids or anhydrides are often used in combination with aromatic and/or saturated aliphatic dicarboxylic acids or the anhydrides derived therefrom, such as phthalic acid, phthalic anhydride, isophthalic acid, tetrachlorophthalic acid, malonic acid, adipic acid, sebacic acid, tartaric acid, and the like.

Unsaturated polyesters containing vinyl groups or vinylidene groups may be obtained by polycondensation of alpha,beta-unsaturated monocarboxylic acids such as acrylic or methacrylic acid, with mono-, di- or polyhydric alcohols. Exemplary alcohols include methanol, ethanol, isopropanol, cyclohexanol, phenol, ethylene glycol, propylene glycol, 2,2-bis(4-hydroxyphenyl)propane, 2,2-bis(4-hydroxycyclohexyl)propane, 2,2-bis(4-beta-hydroxyethyloxy-phenyl)propane, pentaerythritol and dimers thereof, trimethol propane and a glycerol, and the complex diols or polyols. Unsaturated polyesters containing vinyl groups or vinylidene groups also may be obtained by reacting alpha,beta-unsaturated monocarboxylic acids with compounds containing epoxy groups, such as bisphenol A bis(glycidyl ether).

Further, the unsaturated polyesters can be dissolved in monomers copolymerizable with the polyester, which contain one or more C=C groups such as styrene, vinyl toluene, methylmethacrylate, ethyleneglycolmethacrylate, and the like, as is also conventional.

Conventional polyurethane resins are also known in the art and may be obtained by reaction of a polyisocyanate, such as toluene diisocyanate, diphenylmethane diisocyanate, hexamethylene diisocyanate, and the like, with an appropriate compound containing at least two active hydrogen atoms, such as a polyol or a polyamine. Exemplary polyols include ethylene glycol, diethylene glycol, triethylene glycol, trimethylene glycol, propylene glycol, pentaerythritol, and other diols or polyols. Urethane polymers may be used in the form of homopolymers or, more preferably, with various other monomers which can be copolymerized therewith. For example, urethane polymers can be prepared by reacting any of a variety of acrylic comonomers, such as acrylic and methacrylic acids, and their amides, esters, salts and corresponding nitriles, with the polyurethane resin. Particularly suitable comonomers for such polymers are methyl methacrylate, ethyl acrylate and acrylonitrile.

Unsaturated epoxy resins known in the art include those obtained by reaction of an epoxide group (resulting from the union of an oxygen atom with two other atoms, usually carbon), such as epichlorohydrin, oxidized polyolefins, for example ethylene oxide, with an aliphatic or aromatic alcohol such as bisphenol A, glycerol, etc. As with the unsaturated polymers described above, the epoxy resins may be used in the form of homopolymers or copolymers with various other comonomers which can be reacted therewith, including various acrylic monomers, such as acrylic and methacrylic acids, and their amides, esters, salts and corresponding nitrites.

Exemplary monomers and oligomers derived from acrylic and methacrylic acid include acrylic and methacrylic acids, and their amides, esters, salts and corresponding nitrites. Examples include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Other ethylenically unsaturated or vinyl monomers, such as vinyl acetate, vinyl and vinylidene halides and amides, i.e., methacrylamide, acrylamide, diacetone acrylamide, vinyl and vinylidene esters, vinyl and vinylidene ethers, vinyl and vinylidene ketones, olefins, and in particular conjugated diolefins such as butadiene, isoprene, piperylene and 2,3-dimethyl butadiene, vinyl aromatics, i.e., styrene, alkyl styrenes, halostyrenes, alkoxystyrenes, divinyl benzenes, vinyl toluene, and the like are also included. Prepolymers include acrylated epoxides, polyesters and polyurethanes, as described above, and are typically combined with a suitable monomer for viscosity control.

The polymerizable compositions may also contain other conventional agents, such as polymerization inhibitors, fillers, ultraviolet absorbers, organic peroxides, dyes, pigments, and the like.

The polymerizable compositions can be applied or deposited on a surface of a substrate using conventional techniques and apparatus. The substrate to be coated can be, for example, metal, wood, mineral, glass, paper, plastic, fabric, ceramic, and the like. The composition can be applied as a substantially continuous film. Alternatively, the composition can be applied in a discontinuous pattern. The thickness of the deposited composition can vary, depending upon the desired thickness of the resultant cured product. Polymerization can be initiated as known in the art, for example, by exposure to radiation (ultraviolet, electron beam), heat, and the like.

The present invention will be further illustrated by the following non-limiting examples.

Example of stability measurement on a stabilized NPAL sample

A 1.50 gram weighed sample of NPAL stabilized by storage in the presence of a stabilizing agent as noted in the table below is placed in a 125 mL Erlenmeyer flask, and 28.5 grams of toluene is added. The flask is stoppered and swirled until the solid NPAL dissolves to produce a 5% solution. The solution appears light yellow and clear which indicates no insolubles are present. An aliquot of the solution is placed into a 10 mm sample cell of a calibrated Hunter Lab Color Quest II instrument and a measurement taken resulting in a Gardner color of 2.2. Alternatively, a less precise measurement of Gardner color can be done by visual comparison of the sample in a 10 mm tube against a standard set of Gardner color 10 mm tubes. Using this method a Gardner color of 2 is obtained.

Example of stability measurement on a unstabilized NPAL sample

A 1.50 gram sample of NPAL taken from a lot which had been stored at 60° C. without a stabilizing agent was placed in a 125 mL Erlenmeyer, and 28.5 grams of toluene was added. The flask was stoppered and swirled to produce a dark brown cloudy mixture. The mixture was filtered and the resulting filter paper was dried and weighed. The weight of insolubles was found to be 0.9 grams which is 60% of the original weight of NPAL. The filtrate was placed in a 10 mm sample cell of a calibrated Hunter Lab Color Quest II instrument and a measurement taken resulting in a Gardner color of 15.4.

The following table outlines various stabilizing agents and amounts used and the resultant NPAL sample properties of toluene insolubles and Gardner color.

90 Day Storage Results of Stabilized vs. Unstabilized NPAL

| NPAL Sample Description | Appearance of 5 wt % solution | Toluene Insolubles as % of NPAL wt. | Gardner Color of 5% toluene sol'n. |
|---|---|---|---|
| Initial sample before storage | Clear, light yellow | 0 | 2.2 |
| Stored at 60° C. for 90 days in closed vial w/o stabilizer | Cloudy, dark brown | 60% | 15.4 |
| Stored at 60° C. for 90 days in closed vial with 20 wt % molecular sieves | Clear, light yellow | 0 | 2.2 |
| Stored at 60° C. for 90 days in closed vial with 5 wt % molecular sieves | Clear, light yellow | 0 | 2.0 |
| Stored at 60° C. for 90 days in closed vial with 1 wt % molecular sieves | Clear, light yellow | 0 | 2.4 |
| Stored at 60° C. for 90 days in closed vial with 20 wt % powdered carbon | Clear, light yellow | 0 | 2.0 |
| Stored at 60° C. for 90 days in closed vial with 20 wt % granular carbon | Clear, light yellow | 0 | 2.1 |

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

Although specific terms are employed herein, they are used in a generic and descriptive sense only and not for purposes of limitation.

That which is claimed:

1. A stabilized N-nitrosohydroxylamine comprising at least one N-nitrosohydroxylamine in the presence of at least one stabilizing agent capable of binding vapors.

2. The stabilized N-nitrosohydroxylamine of claim 1, wherein said stabilizing agent comprising a hygroscopic substance capable of adsorbing moisture.

3. The stabilized N-nitrosohydroxylamine of claim 1, wherein said stabilized N-nitrosohydroxylamine exhibits a Gardner Index color of no greater than about 4 after being stored at a temperature of 60° C. for 90 days.

4. The stabilized N-nitrosohydroxylamine of claim 1, wherein said stabilized N-nitrosohydroxylamine exhibits a Gardner Index color of no greater than about 2.5 after being stored at a temperature of 60° C. for 90 days.

5. The stabilized N-nitrosohydroxylamine of claim 1, wherein said stabilized N-nitrosohydroxylamine has essentially no toluene insolubles after being stored at a temperature of 60° for 90 days.

6. The stabilized N-nitrosohydroxylamine of claim 1, wherein said N-nitrosohydroxylamine comprises a metallic complex of N-nitrosohydroxylamines.

7. The stabilized N-nitrosohydroxylamine of claim 6, wherein said N-nitrosohydroxylamine comprises at least one metal salt of N-nitrosohydroxylamine of the formula

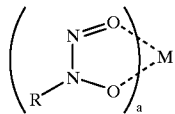

wherein:
  each R is independently selected from the group consisting of alkyl, substituted alkyl, aryl and substituted aryl;
  M is a metal; and
  a is 1 to 4.

8. The stabilized N-nitrosohydroxylamine of claim 7, wherein M is a metal selected from the group consisting of alkali metal, alkali earth metals, Group IIIA metals, Group IVA metals, Group IB metals, Group VIII metals, Group IVB metals, Group VB metals, Group VIB metals, and Group VIIB metals.

9. The stabilized N-nitrosohydroxylamine of claim 8, wherein M is aluminum.

10. The stabilized N-nitrosohydroxylamine of claim 1, wherein said stabilizing agent comprises at least one agent selected from the group consisting of molecular sieves, activated carbon, sulfate salts, silica and mixtures thereof.

11. The stabilized N-nitrosohydroxylaniine of claim 10, wherein said stabilizing agent comprises at least one agent selected from the group consisting of molecular sieves, activated carbon, and mixtures thereof.

12. The stabilized N-nitrosohydroxylamine of claim 1, wherein said stabilizing agent is present in an amount ranging from about 0.1% to about 25% by weight based on the weight of said N-nitrosohydroxylamine.

13. The stabilized N-nitrosohydroxylamine of claim 12, wherein said stabilizing agent is present in an amount ranging from about 0.5% to about 5% by weight based on the weight of said N-nitrosohydroxylamine.

14. A stabilized N-nitrosohydroxylamine comprising at least one N-nitrosohydroxylamine metal salt of the formula

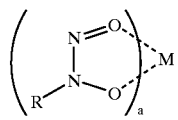

wherein:
  R is aryl or substituted aryl;
  M is a metal; and
  a is 1 to 4,
in the presence of at least one agent selected from the group consisting of molecular sieves, activated carbon, and mixtures thereof.

15. The stabilized N-nitrosohydroxylamine of claim 14, wherein M is aluminum, R is phenyl and said stabilizer comprises a molecular sieve.

16. A container of stabilized N-nitrosohydroxylamine, comprising a container, at least one N-nitrosohydroxylamine and at least one stabilizing agent capable of binding vapors.

17. The container of claim 16, wherein said stabilizing agent comprising a hygroscopic substance capable of adsorbing moisture.

18. The container of claim 16, wherein said stabilized N-nitrosohydroxylamine exhibits a Gardner Index color of no greater than about 4 after being stored at a temperature of 60° C. for 90 days.

19. The container of claim 18, wherein said stabilized N-nitrosohydroxylamine exhibits a Gardner Index color of no greater than about 2.5 after being stored at a temperature of 60° C. for 90 days.

20. The container of claim 16, wherein said stabilized N-nitrosohydroxylamine has essentially no toluene insolubles after being stored at a temperature of 60° for 90 days.

21. The container of claim 16, wherein said N-nitrosohydroxylamine comprises a metallic complex of N-nitrosohydroxylamine.

22. The container of claim 21, wherein said N-nitrosohydroxylamine comprises at least one metal salt of N-nitrosohydroxylamine of the formula

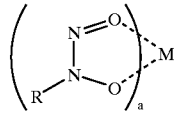

wherein:
  each R is independently selected from the group consisting of alkyl, substituted alkyl, aryl and substituted aryl;
  M is a metal; and
  a is 1 to 4.

23. The container of claim 22, wherein M is a metal selected from the group consisting of alkali metal, alkali earth metals, Group IIIA metals, Group IVA metals, Group IB metals, Group VIII metals, Group IVB metals, Group VB metals, Group VIB metals, and Group VIIB metals.

24. The container of claim 23, wherein M is aluminum.

25. The container of claim 16, wherein said stabilizing agent comprises at least one agent selected from the group consisting of molecular sieves, activated carbon, sulfate salts, silica and mixtures thereof.

26. The container of claim 25, wherein said stabilizing agent comprises at least one agent selected from the group consisting of molecular sieves, activated carbon, and mixtures thereof.

27. The container of claim 16, wherein said stabilizing agent is present in an amount ranging from about 0.1% to about 25% by weight based on the weight of said N-nitrosohydroxylamine.

28. The container of claim 16, further comprising a separate porous container therein in which said at least one stabilizing agent is placed.

29. A process for stabilizing N-nitrosohydroxylamine, comprising placing N-nitrosohydroxylamine in the presence of at least one stabilizing agent capable of binding vapors.

30. The process of claim 29, wherein said stabilizing agent comprising a hygroscopic substance capable of adsorbing moisture.

31. The process of claim 29, wherein said stabilized N-nitrosohydroxylamine exhibits a Gardner Index color of no greater than about 4 after being stored at a temperature of 60° C. for 90 days.

32. The process of claim 29, wherein said stabilized N-nitrosohydroxylamine exhibits a Gardner Index color of no greater than about 2.5 after being stored at a temperature of 60° C. for 90 days.

33. The process of claim 29, wherein said stabilized N-nitrosohydroxylamine has essentially no toluene insolubles after being stored at a temperature of 60° for 90 days.

34. The process of claim 29, wherein said N-nitrosohydroxylamine comprises a metallic complex of N-nitrosohydroxylamines.

35. The process of claim 34, wherein said N-nitrosohydroxylamine comprises at least one metal salt of N-nitrosohydroxylamine of the formula

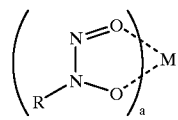

wherein:

each R is independently selected from the group consisting of alkyl, substituted alkyl, aryl and substituted aryl;

M is a metal; and a is 1 to 4.

36. The process of claim 35, wherein M is a metal selected from the group consisting of alkali metal, alkali earth metals, Group IIIA metals, Group IVA metals, Group IB metals, Group VIII metals, Group IVB metals, Group VB metals, Group VIB metals, and Group VIIB metals.

37. The process of claim 36, wherein M is aluminum.

38. The process of claim 29, wherein said stabilizing agent comprises at least one agent selected from the group consisting of molecular sieves, activated carbon, sulfate salts, silica and mixtures thereof.

39. The process of claim 38, wherein said stabilizing agent comprises at least one agent selected from the group consisting of molecular sieves, activated carbon, and mixtures thereof.

40. The process of claim 29, wherein said stabilizing agent is present in an amount ranging from about 0.1% to about 25% by weight based on the weight of said N-nitrosohydroxylamine.

41. A stabilized metal complex of N-nitrosohydroxylamine having a Gardner Index color of no greater than about 4 after being stored at a temperature of 60° C. for 90 days.

42. A stabilized metal complex of N-nitrosohydroxylamine having essentially no toluene insolubles after being stored at a temperature of 60° for 90 days.

* * * * *